(12) United States Patent
Rodriquez-Villegas et al.

(10) Patent No.: US 8,855,758 B2
(45) Date of Patent: Oct. 7, 2014

(54) APPARATUS AND METHOD FOR OBTAINING EEG DATA

(75) Inventors: Esther O. Rodriquez-Villegas, London (GB); David C. Yates, Lancashire (GB)

(73) Assignee: Imperial Innovations Limited, London (GB)

( * ) Notice: Subject to any disclaimer, the term of this patent is extended or adjusted under 35 U.S.C. 154(b) by 476 days.

(21) Appl. No.: 12/375,765

(22) PCT Filed: Aug. 2, 2007

(86) PCT No.: PCT/GB2007/002953
§ 371 (c)(1),
(2), (4) Date: Mar. 23, 2009

(87) PCT Pub. No.: WO2008/015449
PCT Pub. Date: Feb. 7, 2008

(65) Prior Publication Data
US 2009/0312664 A1    Dec. 17, 2009

(30) Foreign Application Priority Data
Aug. 3, 2006   (GB) .................................. 0615463.7

(51) Int. Cl.
*A61B 5/04* (2006.01)
*A61B 5/0476* (2006.01)
*H03F 3/45* (2006.01)
*A61B 5/00* (2006.01)

(52) U.S. Cl.
CPC .............. *A61B 5/0476* (2013.01); *A61B 5/0002* (2013.01); *H03F 2200/375* (2013.01); *A61B 5/7232* (2013.01); *H03F 2203/45044* (2013.01); *A61B 5/726* (2013.01); *H03F 3/45995* (2013.01)

USPC ........... 600/544; 600/545; 600/509; 600/523; 600/383; 600/302

(58) Field of Classification Search
USPC ......... 600/383, 509–523, 302–308, 345–371, 600/481–507, 529–545
See application file for complete search history.

(56) References Cited

U.S. PATENT DOCUMENTS 4,417,590 A * 11/1983 Smith et al. .................... 600/544
4,498,080 A *  2/1985 Culver .......................... 345/671
4,610,259 A *  9/1986 Cohen et al. .................. 600/544
(Continued)

FOREIGN PATENT DOCUMENTS

WO       WO-/00/25668       5/2000

OTHER PUBLICATIONS

Argoud et al., "SADE3 an effective system for automated detection of epileptiform events in long-term EEG based on context information", Med Biol Eng Comput (2006). (Provided by Applicant in IDs).*

(Continued)

*Primary Examiner* — Christine Matthews
*Assistant Examiner* — Sunita Reddy
(74) *Attorney, Agent, or Firm* — Dickstein Shapiro LLP

(57) ABSTRACT

An apparatus for obtaining EEG data includes a signal processing component for receiving EEG signals from each of a plurality of electrodes and a data output component. The signal processing component is arranged to convert respective EEG signals in real time to a reduced data set and provide the reduced data set to the data output component.

17 Claims, 7 Drawing Sheets

(56) References Cited

U.S. PATENT DOCUMENTS

| | | | |
|---|---|---|---|
| 5,279,305 A * | 1/1994 | Zimmerman et al. | 600/544 |
| 2002/0052539 A1 * | 5/2002 | Haller et al. | 600/300 |
| 2002/0165437 A1 * | 11/2002 | Chen | 600/300 |
| 2003/0225342 A1 * | 12/2003 | Hong et al. | 600/558 |
| 2004/0199482 A1 | 10/2004 | Wilson | |
| 2006/0089112 A1 * | 4/2006 | Irazoqui-Pastor et al. | 455/130 |
| 2006/0116738 A1 * | 6/2006 | Wolf et al. | 607/45 |
| 2007/0208235 A1 * | 9/2007 | Besson et al. | 600/301 |
| 2007/0276270 A1 * | 11/2007 | Tran | 600/508 |
| 2008/0082019 A1 * | 4/2008 | Ludving et al. | 600/544 |

OTHER PUBLICATIONS

Harrison and C. Charles, "A low-power low-noise CMOS amplifier for neural recording applications", IEEE Journal of Solid-State Circuits, vol. 38, No. 6, pp. 958-965, Jun. 2003.*

Niels Coninx, "Automated Detection of Epileptic Events in the Interictal EEG Using the Wavelet Transform" Bachelors Thesis, University of Maastricht, Jun. 17, 2005.

Lim et al., "A Low-Power and Low-Offset CMOS Front-End Amplifier for Portable EEG Acquisition System", 2004 IEEE International Workshop on Biomedical Circuits & Systems.

Moreno et al., "Towards a Knowledge based System for the Clinical Evaluation of the Electroencephalogram and Visual Evoked Potentials", 1998 IEEE.

Antoniol et al., "EEG Data Compression Techniques", IEEE Transactions on Biomedical Engineering, vol. 44, No. 2, Feb. 1997.

Gopikrishna et al., "A High Performance Scheme for EEG Compression Using a Multichannel Model", Department of Electrical Communication Engineering, Indian Institute of Science.

Argoud et al., "SADE[3]: an effective system for automated detection of epileptiform events in long-term EEG based on context information", Med Biol Eng Comput (2006).

Gotman, G.; *Practical Use of Computer-Assisted EEG Interpretation in Epilepsy*, Journal of Clinical Neurophysiology 1985; pp. 251-265.

Obeid, I, et al.; *Evaluation of Spike-Detection Algorithms for a Brain-Machine Interface Application*; IEE Transactions on Biomedical Engineering, vol. 51, No. 6, Jun. 2004; pp. 905-911.

* cited by examiner

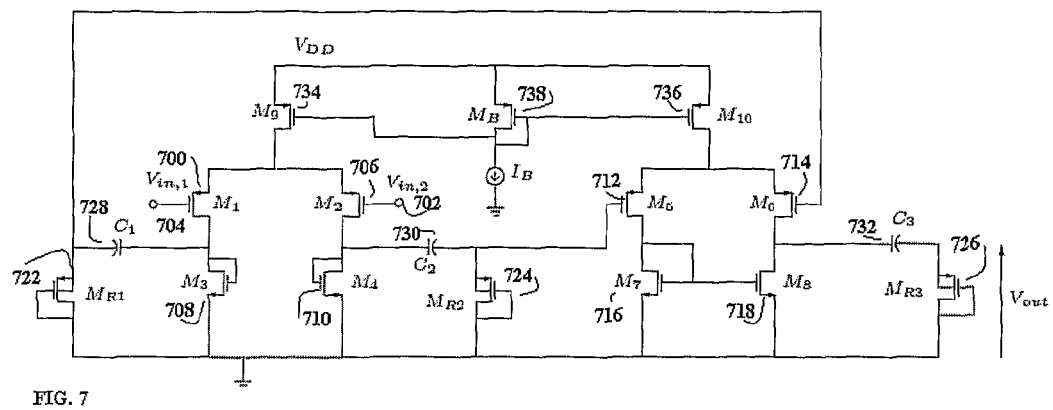
FIG. 7
FIG. 8
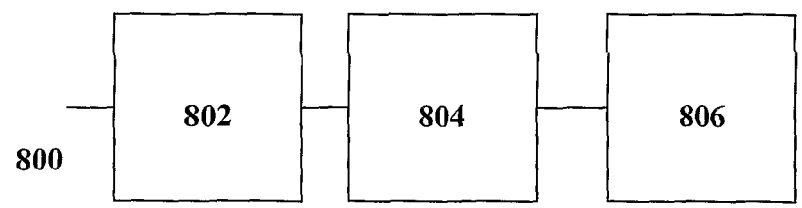

APPARATUS AND METHOD FOR OBTAINING EEG DATA

The invention relates to an apparatus and method for obtaining EEG data.

About 1% of the world's population suffers from the chronic neurological condition known as epilepsy. Over 2.5 million are affected in the USA and 350,000 in the UK, where 30,000 will develop the disease each year. Despite treatment with antiepileptic drugs, 40-50% of people with epilepsy continue to experience seizures or severe side effects.

Eletroencephalography (EEG) plays a vital role in the diagnosis and treatment of neurological diseases such as epilepsy. Often patients are simply monitored in-house with hard-wired cumbersome equipment for no more than 24 hrs, resulting in limited data for diagnosis and treatment. Continuous (or regular) long-term monitoring of patients in their everyday environment has the potential to significantly improve both diagnosis and treatment. Longer term patterns and underlying causes will be more surely recognised by the neurologist, the effectiveness of current medication more accurately monitored and the dosage more assuredly controlled. Furthermore long-term continuous monitoring leads to the possibility of forewarning the patient through seizure prediction and even to the prevention of seizure through some action, such as neural stimulation.

Monitoring patients in their home environment is possible using commercially available Ambulatory EEG (AEEG) systems. Electrodes attached to the patient's head, are connected to the recording unit, usually worn on a belt or over-the-shoulder pouch. Most models weigh about 1 kg, including battery pack and hard drive, are about the size of a portable CD player and usually record 24 hours of data.

Other applications in which EEG monitoring is used include monitoring and diagnosis of sleep disorders such as sleep apnoea.

EEG monitoring is not just of use for detecting abnormal health states but may also be used to determine a person's emotional state and can be used in determining if a person is, for example, bored, tired, stressed or angry. Such monitoring may aid in allowing, for example, improved reactions to barrages of data for people such as pilots and improved control of prosthetic limbs by electronically transferring thoughts into operating signals.

The basic structure of conventional EEG monitoring approaches can be further understood with reference to FIG. 1 which shows a plurality of electrodes 100a, 100b, 100c placed on a layer of tissue 102 such as the scalp which receives signals such as EEG signals. The analogue signals are passed through an amplifier and conversion circuit 104, converting them to digital signals which are then stored in the memory 106. The stored digitised data is downloaded subsequently for analysis at step 108.

However the current AEEG systems can cause significant discomfort in the wearer because of their weight and bulk.

The invention is set out in the claims. In particular because of the provision of an apparatus for obtaining EEG data including a signal processing component for converting EEG signals in real time to a reduced data set, the power requirements are reduced. In one aspect because of the provision of a reduced data set, the amount of data is reduced such that wireless transmission is possible in conjunction with acceptable battery or power source lifetime.

Embodiments of the invention will now be described, by way of example, with reference to the drawings, of which:

FIG. 7 shows in more detail the circuit design of a chopper differential amplifier;

FIG. 8 is a block diagram showing the components of a feature extraction circuit according to the present approach.

Figure 1:
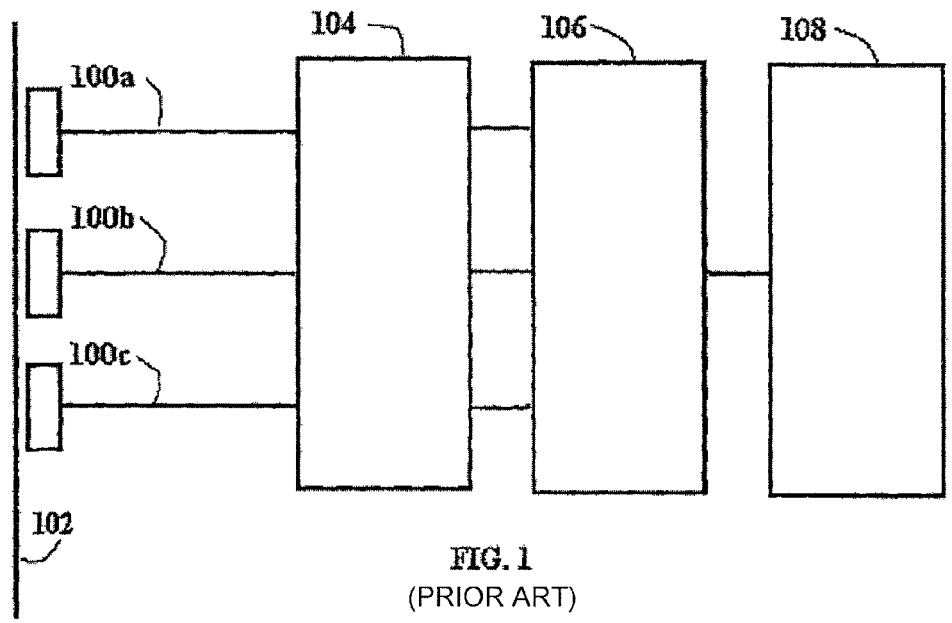
FIG. 1 is a block diagram showing the structure of a prior art AEEG system.
Figure 2A:
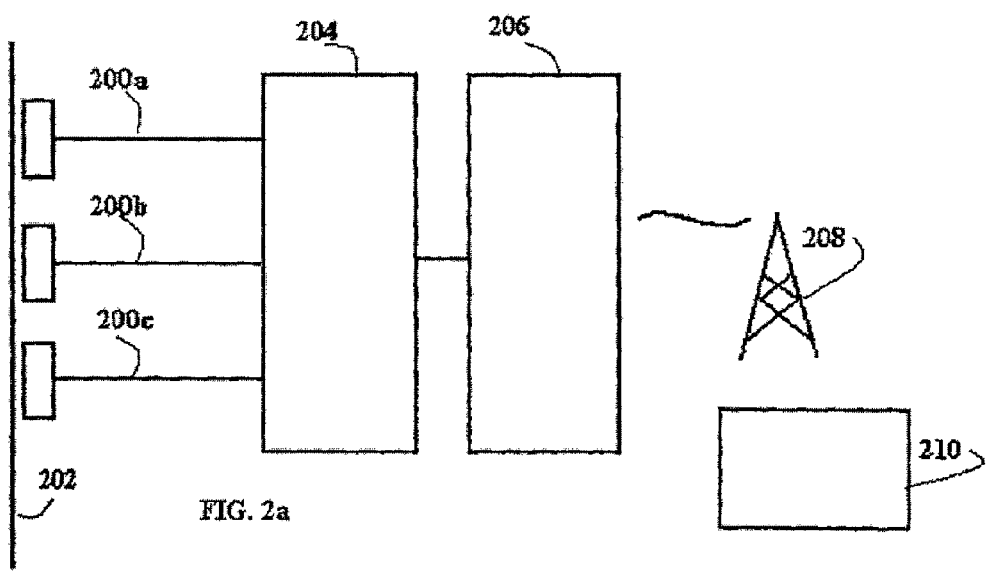
FIG. 2a is a block diagram showing an AEEG system according to the approach described herein.

In overview the invention can be further understood with reference to the block diagram of FIG. 2a. A plurality of electrodes 200a, 200b, 200c are placed against tissue such as the scalp 202. A signal processing component 204 which, as described in more detail below, and which can be realised partially or entirely in analogue components receives the analogue EEG signals from the electrodes. The signal processing component 204 converts the received EEG signals to a reduced data set, that is, to a reduced amount of data whilst ensuring that the retained data does not miss EEG information that could be of relevance for the particular application. For example, if the system is used for monitoring of epilepsy the signal processing unit identifies sections of data that are clearly not representative of epileptic activity and keeps those sections of data that might be. In example applications related to monitoring of cognitive states such as fatigue, drowsiness, stress, workload, memory, attention, relevant sections of data may be those containing brainwave features that are indicative of the user's cognitive state.

In order to minimise battery size, low power circuits and systems are implemented allowing wireless transmission of the reduced EEG data set. As discussed in more detail below, two principal approaches are implemented.

Firstly the offset voltage generated at the electrode tissue interface (202) may be removed from the signal. This reduces the required resolution by, for example, over 6 bits, reducing the amount of digitised data. This may be implemented if the circuitry required to remove the offset consumes less power than the extra power required by the other circuit blocks to deal with the increased dynamic range (i.e. increased number of bits, typically 6 bits).

Secondly local signal processing techniques are implemented rather than storing all of the data for subsequent processing. The signal processing techniques, which are typically performed in real-time, are applied to the data subsequent to removal of the offset voltage, include a feature extraction step for recognition and isolation of significant EEG signal events and ensuring that the data set is restricted to events of importance. Additionally, data compression techniques are applied to reduce the amount of data whilst losing little or no information.

The reduced data set is then provided to a data output component 206 which can be a data output to a storage device such as a disk or hard drive or, in an optimisation, a wireless transmitter to a wireless receiver 208 connected to a base station 210 which can be, for example, a monitoring computer or a screen viewed by the healthcare specialist.

Such a wireless configuration, which dominates the power consumption, is enabled according to the approach described herein because of the reduced data set and hence the reduced power requirements in transmitting less data. For example current state of the art low power wireless transceivers attempting to send the full data set would drain a single miniature coin cell in less than a few hours at the data rates in conventional EEG devices.

Figure 2B:
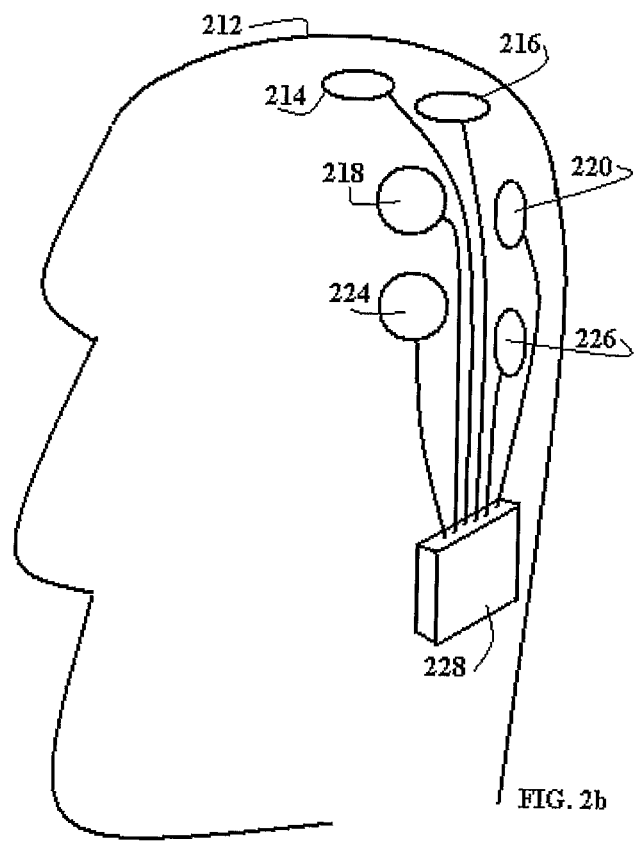
FIG. 2b is a first example schematic diagram showing a mounted AEEG system.
Figure 2C:
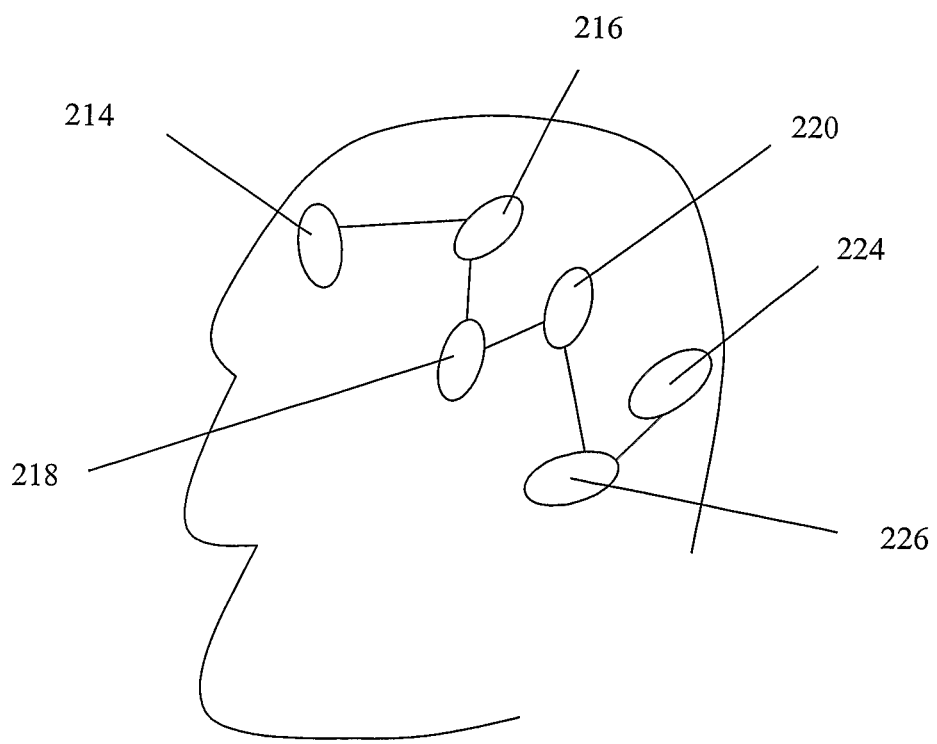
FIG. 2c is a second example schematic diagram showing a mounted AEEG system.

In the event that the data is not stored then the hard disc or other storage device typically worn by the patient in conventional devices can be dispensed with. This has the further benefit that the storage capacity of the existing devices is no longer a limiting factor for example requiring the user to upload the data from a full storage disk before monitoring can continue. Similarly the connecting wires to the hard disk which might typically be worn on the belt or in a shoulder pouch can be dispensed with. Hence the device can be made more lightweight, less bulky and less obtrusive ensuring that it can be worn more comfortably regularly or continuously enabling continuous long term monitoring. For example as shown in FIG. 2b and FIG. 2c the entire apparatus can be mounted on the head 212 rather than requiring wires trailing down to additional bulky components elsewhere on the wearer's body. In particular electrodes 214, 216, 218, 220, 224, 226 may be mounted on the head and connected to housing 228 mounted on the user's head or neck and containing the power, signal processing and data output components. This configuration is shown in FIG. 2b. Alternatively, as shown in FIG. 2c, the circuitry and batteries may be distributed across the head hence distributing also the weight to optimize the user's comfort. For example, some circuitry could be present in each electrode 214, 216, 218, 220, 224, 226 or in a subset of the electrodes 214, 216, 218, 220, 226.

The low power requirements are enhanced yet further by the provision of some or all of the processing components in analogue—for example for systems requiring a signal to noise ratio of no more than approximately 80 dB (13 bits) the power consumption of an analogue implementation can be less than an equivalent digital implementation.

Figure 3:
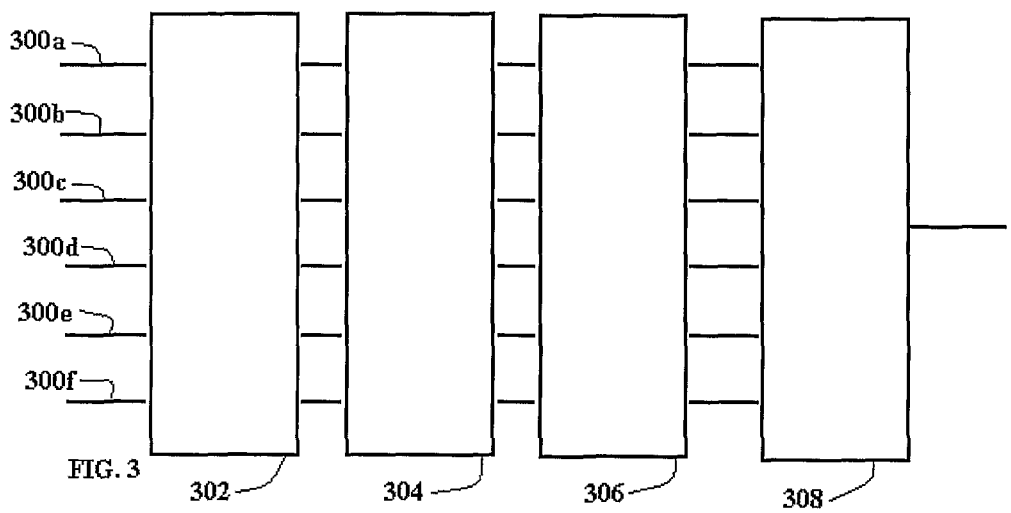
FIG. 3 is a block diagram showing in more detail the components of a signal processing component of an AEEG according to the approach described herein.

Turning to more detailed aspects of the invention, the components of the signal processing circuit can be further understood with reference to FIG. 3. One or more EEG signals are received over lines 300a to 300f from respective electrodes—it will be appreciated that any number of electrodes and corresponding signals can be processed as appropriate. The input signals go to a voltage offset reduction component at block 302 before being passed to an initial processing step at block 304 where the signals are amplified, the features of which are described in more detail below. In particular the voltage offset reduction circuit 302 removes the voltage offset to reduce the data set, which step can be implemented using analogue components such as chopper amplifiers.

Each of the received signals is forwarded on with the DC offset removed to a feature extraction component in block 306. The feature extraction component uses local signal processing algorithms to detect important events for example filtering known EEG profiles which will be of interest to the neurologist or automatic analysis tool, reducing the overall power consumption as well as the burden on the neurologist who does not have to view unimportant data.

The further reduced data set comprising the extracted features is then forwarded to a data compression component 308. Various data compression approaches can be used, for example comparing respective reduced EEG signals and outputting a reduced data set representing a correlation between respective EEG signals. For example a base EEG signal can be output or transmitted together with respective additional signals for other channels simply representing the difference between each of those channels and the base signal. In view of the correlation that is typically observed between signals received from EEG electrodes on different parts of the scalp, it is found that significant data reduction can be achieved in this way. The approach can be further improved by identifying either automatically or heuristically sub-groups of electrodes, for example located in common regions of the scalp, which are likely to demonstrate high levels of correlation.

The voltage offset reduction component assuming for illustration purposes a signal coming from only one electrode, can be further understood with reference to FIGS. 4 to 7. A schematic EEG signal 400 is shown in FIG. 4A as incorporating a DC offset. Scalp EEG signals exhibit typical amplitudes between about one micro volt and 500 micro volts at typical frequencies below about 30 Hertz. The EEG electrodes generate DC offset voltages typically in the range of 10's of mV. Being about 1000 times the actual signal, this DC offset will dominate the dynamic range if it is not rejected before amplification The performance of the front end amplifier is key therefore to the data acquisition system meeting power, voltage supply and noise constraints combined with a signal dominated by offset. An rms input referred noise voltage of less than 2 μV is required for a dynamic range of 8 bits. The gain should be between 40 dB and 50 dB to achieve the required resolution whilst ensuring that the amplifier does not saturate. The current drain should be no more than a few microamps at 1 V supply and the large DC offset must be rejected in order to achieve the required dynamic range.

According to a specific embodiment the circuit is implemented using complementary metal oxide semi conductor, (CMOS) technology which is particularly suitable for low cost, low power system—on-a-chip solutions. However such systems exhibit high flicker noise.

Figure 4A:
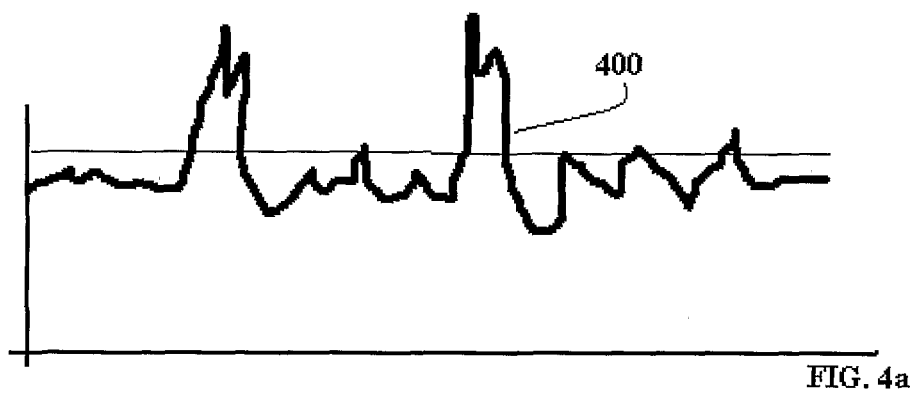
FIG. 4a shows an EEG trace with DC offset.
Figure 4B:
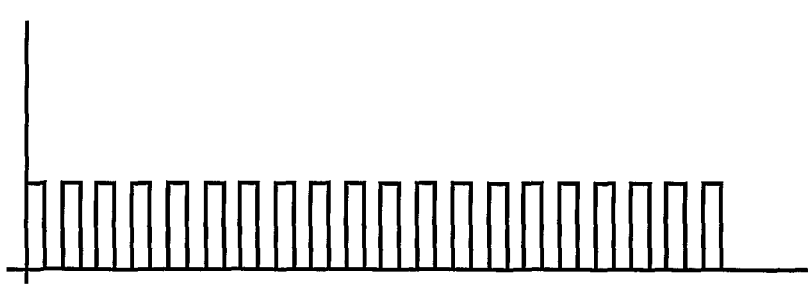
FIG. 4b shows the choppper signal from complementary halves of a chopper input circuit.
Figure 4B:
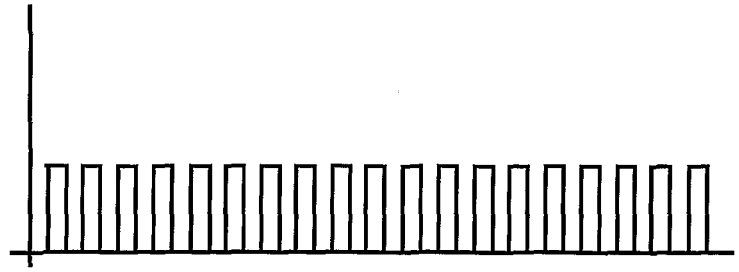
Figure 4C:
FIG. 4c shows modulation of the EEG signal of FIG. 4a by the chopper signal of FIG. 4b.
Figure 4D:
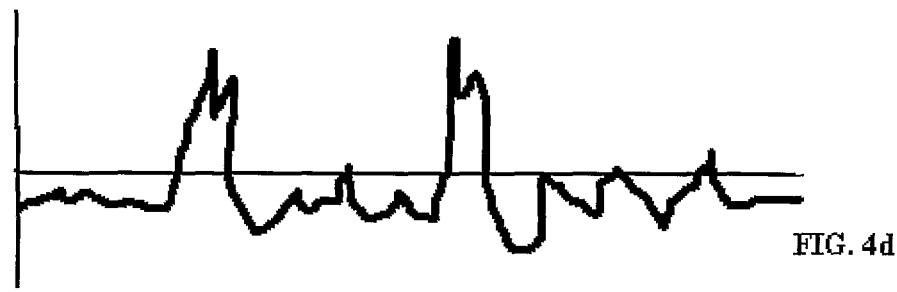
FIG. 4d shows the reconstituted EEG signal with DC offset removed.

Accordingly the present approach implements, in one non-limiting embodiment, a "chopper" amplifier. Such amplifiers will be known in general to the skilled reader and the general operation can be understood with reference to FIGS. 4b to 4d. Referring to FIG. 4b it can be seen that complementary out-of-phase chopper frequencies comprising square wave pulses are generated at a chop frequency $f_c$. The EEG signal is modulated prior to amplification with the square wave at the chop frequency which, ideally, is set to a frequency at which the flicker noise is negligible. As shown in FIG. 4c the modulated signals are added and after amplification at the chop frequency $f_c$ the signal is downconverted to base band whilst flicker noise and any amplifier offset voltages are simultaneously up converted to the chop frequency where they can be filtered out. Accordingly the signal is effectively extracted from the modulated signal of FIG. 4c to provide the signal of FIG. 4d without DC offset. It is found that the chopper technique consistently achieves impressive noise performance and that low power operation is possible. However the specific required specifications for an EEG wireless transceiver of the type described herein are not met by prior art designs, and in particular the provision of both low voltage operation, low noise and low power consumption.

Figure 5:
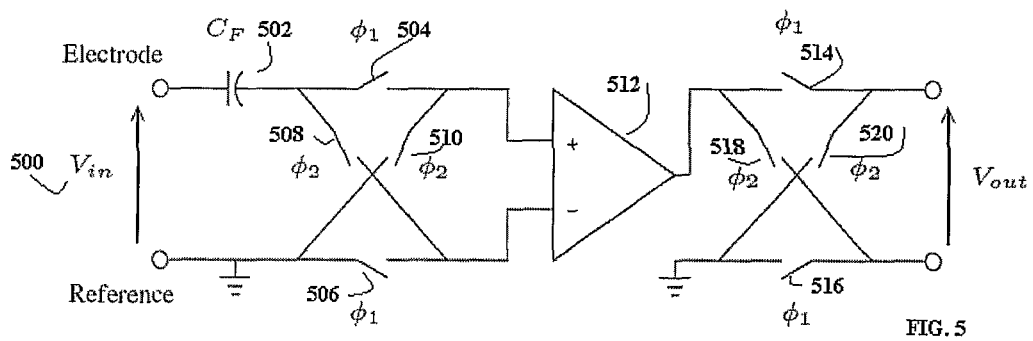
FIG. 5 is a circuit diagram showing a chopper amplifier.

It is found that the circuit of FIG. 5, on the other hand, provides the required architecture, providing a 1 V, 1.4 μW chopper amplifier implemented in a 0.35 am CMOS process. The achieved input referred noise voltage is 1.5 µV rms and the gain is 44 dB. Since the dynamic range of the input EEG signal is dominated by the offset voltage generated at the electrode-tissue interface, an input high pass filter limits the required filter capacitance to 40 pF by recognising that the input chopper switches can be combined with the amplifier input capacitance to emulate a large resistance.

The chopper amplifier receives an input voltage $V_{in}$ 500 across a capacitance $C_f$ and four crosses switches 504, 506, 508, 510 providing a chopper to an amplifier 512. The switches are implemented by four NMOS transistors, driven by non-overlapping anti phase clock signals $\phi_1$ and $\phi_2$, which switch 5 between zero volts and 1 volt at the chop frequency. Four further crossed switches switched at $\phi_1$ and $\phi_2$ are provided to complete the frequency conversion process at the output of the amplifier 512, namely switches 514, 516, 518, 520. The input transistors are preferably of minimal size to reduce charge feed through from the clock signal for example having a width of 0.4 µm but having length 7 µm to reduce the drain current noise of the switches. As the noise contribution of the output switches 514, 516, 518, 520 is negligible they can remain minimum size. In operation the switches $\phi_1$ and $\phi_2$ are operated in anti phase to provide the square wave frequency input shown in FIG. 4b to the amplifier 512, and the output switch $\phi_1$ and $\phi_2$, 514 to 520 similarly are operated in anti-phase to provide the frequency down conversion post amplification.

Rejection of the electrode DC offset before amplification is necessary to achieve the required dynamic range, which is severely limited by the low voltage supply. To minimise the required capacitance for a high pass corner frequency of below 0.5 Hz requires a very large resistance ($R_F > 10^{10} \Omega$ for $C_F \leq 40$ pF). Optimally the high pass filtering takes place before the signal is upconverted to avoid designing a corner frequency between fc and fc+0.5 Hz. Furthermore, no active devices are used before frequency upconversion in order to minimise flicker noise.

Figure 6:
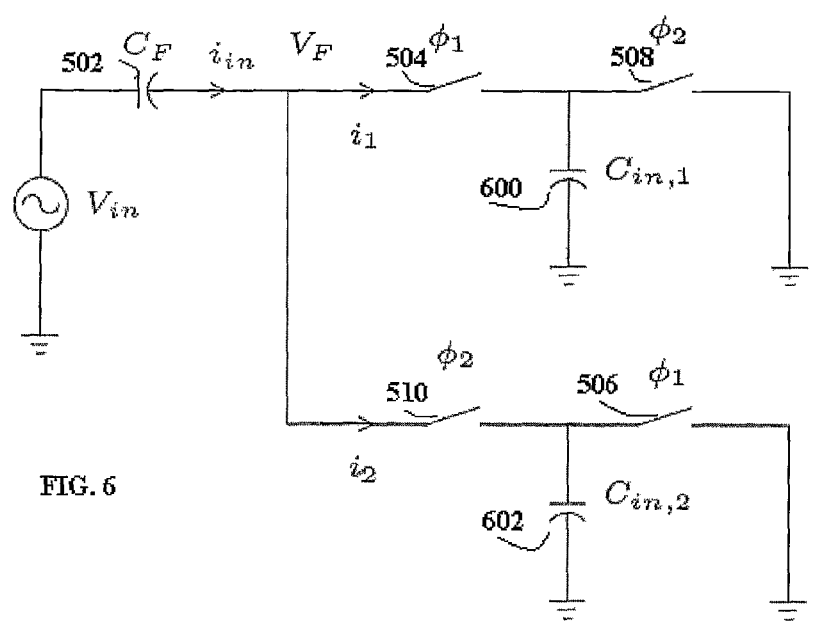
FIG. 6 is a diagram showing an equivalent high pass filter to a chopper differential amplifier.

Prom switched capacitor theory it can be seen that the input chopper switches combined with the input capacitance of the differential amplifier emulate a resistor, $R_F$. The equivalent circuit is shown in FIG. 6. $C_F$ 502 and the effective resistance $R_F$, form a high pass filter. $C_{in,1}$ 600 and $C_{in,2}$ 602 represent the input capacitances of the differential amplifier. The node at which voltage $V_F$ is generated, is biased by the body-source diode of the NMOS input switches. During clock phase $\phi_1$, $C_{in,1}$ 600 is charged to $V_F$, whilst $C_{in,2}$ 602 is discharged to ground. Contrastingly, during $\phi_2$, $C_{in,2}$ is discharged to $V_F$ and $C_{in,1}$ is discharged. The average current $i_{in,ave}$ is given by:

$$i_{in,ave} = i_{1,ave} + i_{2,ave} \quad (1)$$
$$= \frac{C_{in,1}}{T_c} \cdot V_F + \frac{C_{in,2}}{T_c} \cdot V_F$$

Where $T_c$ is the clock time period.
Assuming $C_{in,1} = C_{in,2} = C_{in}$ the equivalent filter resistance, $R_F$, is given by:

$$R_F = \frac{T_c}{2 \cdot C_{in}} \quad (2)$$

A high $R_F$ can be achieved by decreasing the chop frequency and decreasing the size of the differential amplifier input transistors, $M_1$ and $M_2$ as discussed below with reference to FIG. 7.

Hence it will be seen that by appropriate selection of the components both of the chopper switch arrangement and of the differential amplifier 512, a large resistance can be emulated allowing the filter capacitance $C_F$ to be kept as low as 40 pF providing a high pass filter with a 3 dB frequency<0.5 Hz.

The differential amplifier of FIG. 7 comprises a conventional differential amplifier stage of transistors $M_1$, $M_2$ 704, 706 which receive input voltages 700, 702 and are connected to diode connected transistors $M_3$ and $M_4$ which work weak inversion and act as load resistors dimensioned to optimise for low noise. The outputs from the differential amplifier stage are filtered by respective capacitors $C_1$, $C_2$, 728, 730 and loads $M_{R1}$, $M_{R2}$, 722, 724. The outputs are received at input transistors $M_5$, $M_6$, 712, 714 which are connected to respective transistors $M_7$, $M_8$, 716, 718 forming a current mirror. An output voltage is taken between transistors $M_6$ and $M_8$ across a further filter of capacitor $C_3$ 732 and diode connected transistor $M_{R3}$ 726. DC bias conditions to the two stages are provided by respective transistors $M_9$, $M_{10}$, 734, 736 acting as respective current sources in conjunction with a master current source, with transistor $M_{B9}$ 738.

The differential amplifier is thus designed in two stages. The amplifier receives the unconverted signal $V_{in,1}$(700)-$V_{in,2}$(702) directly from the four input chopper switches 504-510. A standard low noise design strategy is to provide high gain in the first stage. Here, however, the first stage has been chosen as a diode connected active load differential pair. The self biasing and low gain of this buffer stage are necessary to enable the input transistors, $M_1$ 304 and $M_2$ 706 to be small without mismatch and process variation causing the amplifier to saturate.

Sizing transistors $M_1$ 704, $M_2$ 706, $M_3$ 708 and $M_4$ 710 is a delicate balance between minimising noise, maintaining a high $R_F$ and ensuring that the gain of $M_1$ $g_{m1}$ is not significantly less than the gain of $M_3$ $g_{m3}$ since the gain of this first stage is $g_{m1}/g_{m3}$. $M_1$ and $M_2$ are minimum length to maximise $R_F$. The width is set to 3.5 µm to allow 250 nA of drain current whilst still in subthreshold $M_3$ and $M_4$ operate in weak inversion, being width 36 µm by length 4 µm. The square of the equivalent gate referred channel noise voltage, $v^2_n$, for a MOS transistor in weak inversion is given by:

$$v_n^2 = \left[ \frac{2kT(1+\eta)}{gm} + \frac{KF}{f \cdot C_{ox}^1 \cdot WL} \right] \cdot \Delta f \quad (3)$$

where k is Boltzmann's constant, T is the absolute temperature, $\eta$ is the ratio of the body-source transconductance, $g_{mbs}$ to the gate-source transconductance, gm, KF is an empirical flicker noise parameter $C^1_{ox}$ is the oxide capacitance per unit area, W is the device width and L is the device length.

The square of the equivalent input referred noise voltage, $v^2_{eq}$, of a MOS differential amplifier is:

$$v_{eq}^2 = v_{n1}^2 + v_{n1}^2 + v_{n2}^2 + \left( \frac{gm3}{gm1} \right)^2 \cdot (v_{n3}^2 + v_{n4}^2) \quad (4)$$

where $v_{nk}$ is the gate referred channel noise voltage of transistor $M_k$.

To minimise noise in this circuit the drain current is increased. The noise is predominantly thermal due to the frequency upconversion process and the transconductance in weak inversion is improved through increased drain current. Unlike strong inversion operation, this results in the ratio of device sizes being unimportant.

Transistors $M_5$ 712, $M_6$ 714, $M_7$ 716, $M_8$ 718 and $M_{10}$ 710 form a second stage differential amplifier which provides the gain. Here the transistors are much larger than those of the first stage to ensure that mismatch and process variation has little effect; $M_5$ and $M_6$ are 72 μm by 10 μm, $M_7$ and $M_8$ are 160 μm by 8 μm. The current through each branch is 400 nA, sufficient for the second stage noise to be insignificant.

The differential output of the first stage is high pass filtered to control the input common mode of the second stage and to reject offset voltage due to mismatch or process variation. The output is also high pass filtered before downconversion. The filtering is done using the diode connected 4 μm by 4 μm PMOS devices, $M_{R1}$ 722, $M_{R2}$ 724, $M_{R3}$ 726, which form an extremely high incremental resistance ($<10^{11}$) in conjunction with capacitors $C_1$ 728, $C_2$ 730, and $C_3$ 732. $C_1$ and $C_2$ are 10 pF and $C_3$ is 1 pF. $C_1$ and $C_2$ are set to the higher value of 10 pF to reduce the capacitive division with the input capacitances of the next stage.

Turning now to FIG. 8 the feature extraction component can be understood in more detail. In particular a signal 800 is received from the voltage offset reduction component described above. In practice, one or multiple such signals would be received, depending on whether the channels have been dealt with individually or some multiplexing strategy has been applied. The spike or expected EEG feature profile is automatically detected in any appropriate manner that will be apparent to the skilled reader such that detailed description is not required here, but one possible approach is using wavelet analysis of the EEG as described in more detail, for example, in Niels Coninx, "Automated Detection of Epileptic Events in the Interictal EEG using the Wavelet Transform", 17 Jun. 2005, Bachelors Thesis, University of Maastricht, which is incorporated by reference herein.

Each signal is passed through a filter 802, whose impulse response is designed to perform the continuous wavelet transform for a mother wavelet chosen to resemble the spike or expected EEG feature profile. To reduce the dependence on the amplitude of the recording the square of the normalised wavelet coefficients are used:

$$\tilde{W}(a,b) = \frac{W^2(a,b)}{\sigma^2}$$

where a and b are the scale and translation parameters, σ is the standard deviation of the signal and W(a,b) is the wavelet coefficient given by the continuous wavelet transform.

The normalised wavelet coefficients are passed to block 804, where they are compared with a predetermined threshold value. If the coefficients exceed this value then an epileptic event is considered to have occurred at the corresponding moment in time for which that wavelet coefficient was generated. Artefacts are identified by comparison of the normalised wavelet coefficient for a mother wavelet scale resembling an epileptic event with the normalised wavelet coefficient for a larger scale which would resemble an artefact. These artefact coefficients are calculated in parallel. If the normalised wavelet coefficient for the artefact is larger then no epileptic event is considered to have occurred.

Different features are detected using different wavelet scales. Combinations of features such as the spike and slow wave are detected using a linear combination of time shifted wavelet coefficients for different scale wavelets:

$$F(a,b) = c_1 W(a,b) + c_2 W(a_s, b+\tau)$$

where $c_1$ and $c_2$ are the predetermined weightings to be applied to each feature, $a_s$ is the wavelet scale for the slow wave and τ is the expected time shift between the two features. All the required scales for the different features are calculated in parallel.

At block 806, the correlated feature which can be identified for example by time matching the point of peak recognition at step 804 with the corresponding feature in the input signal and selecting that feature is extracted and the extracted feature is output to the next stage of the signal processing circuitry as described below.

Hence block 802 implements the filters which perform the continuous wavelet transform for the various mother wavelet scales. Block 804 makes the necessary linear combinations and comparisons to detect epileptic features. Block 806 correlates the feature detection with the original signal deemed to contain an epileptic event. This requires a memory or time delay circuit to allow selection of the appropriate part/feature of the input signal. The specific features can be implemented in digital or analog components as appropriate. For example the filter and impulse response can be implemented in analogue circuitry and the correlation and extraction components can be implemented in digital circuitry.

Figure 9:
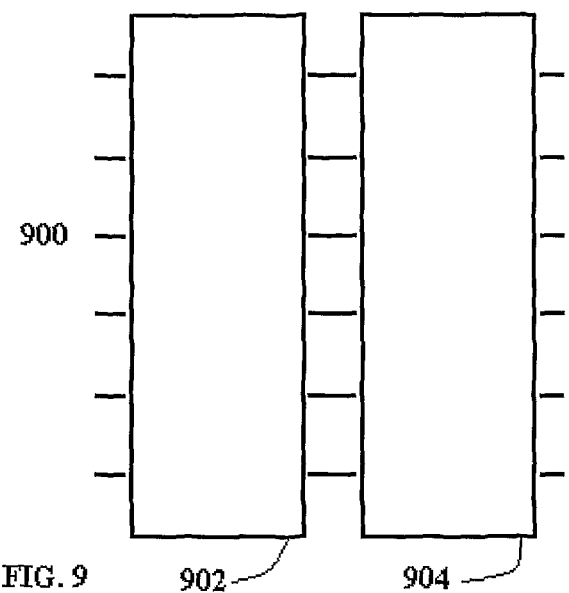
FIG. 9 is a block diagram showing the components of a data compression component according to the present approach.

Turning now to FIG. 9, the components of a data compression component can be seen in more detail. The incoming signal 900 is received and may correspond, for example, to the signal with DC offset removed and only for extracted features per channel. The signal is digitised at analogue to digital converter 902 and each of the digitised channels is received at a comparison component 904. The comparison component compares a base-line signal, which can be for example any nominally selected input channel signal and outputs that signal as a base signal representation together with the difference or delta in each of the compared signals as a difference signal representation. As there is a high level of correlation, the amount of data in the difference signal will be less than that in the original signal from which it was derived. In one approach the signals arriving at the comparison component can be grouped according to pre-determined groupings corresponding, for example, to electrode positionings on the scalp in regions which are known to have strongly correlated EEG activity. The signals can be reconstructed by recombining each of the difference signals with the base signal.

One appropriate EEG compression scheme is described in "A high performance scheme for EEG compression using a multichannel model" of D Gopikrishna et al, Lecture Notes in Computer Science, vol. 2552, pp 443-451, 2002, which is incorporated herein by reference and which discuss capturing interchannel correlation using adaptive filtering.

Groups of correlated EEG channels are related to a single EEG channel using an adaptive filter such as that presented in "A New Adaptive IIR Filter", H. Fan and W Kenneth Jenkins, IEEE Trans. Circuits and Systems, vol. cas-33, no. 10, pp 939-947, October 1986. The single channel signal, x(t), to which the others in the group of correlated EEG channels are to be related is first compressed using the wavelet transform, ready for transmission, and is then reconstructed. This signal, x'(t), is passed into an adaptive filter, which periodically adapts the filter coefficients to reduce the error between the filter output y'(t) and a correlated channel signal, y(t), below a certain preset value. The error signal, e(t), and the filter coefficients are compressed using a standard technique, such as the discrete cosine transform, and are transmitted along with the compressed version of x(t). All the information is then present at the decoder to perfectly reconstruct the original signals.

It will be appreciated once again that the component can be implemented in any appropriate manner for example using analogue or digital techniques as appropriate.

The individual components can be of any appropriate type. For example the EEG electrodes and leads can be any appropriate transceivers providing analogue signals to the signal processing circuitry. The various components of the signal processing circuitry can similarly be fabricated in any appropriate manner and from easily available components as will be apparent to the skilled reader. The data output component can be any appropriate transceiver, again as will be apparent to the skilled reader. All of the components can be mounted or housed using any appropriate approach.

As a result of the arrangement described a low power, low noise, low voltage arrangement is implemented which benefits both from the use of analogue components and provision of a reduced data set to allow long battery lifetimes and a potential for wireless transmission for data in real time. The signal processing component selects application specific features of interest such as epileptic transients in the case of epilepsy monitoring, reducing the amount of data to be transmitted and stored. In the specific case of epilepsy this furthermore saves much time for the physician, who is no longer required to view unimportant data. Data reduction lowers the power consumption, size and weight of an AEEG device.

It will be appreciated that aspects of the approaches described herein can be juxtaposed or interchanged as appropriate and that the approach is not limited to the specific embodiments described above. For example any number of EEG signal channels can be supported and any combination of the components described above can be implemented still effecting a power/data saving. For example any one of the voltage offset reduction component, feature extraction component or data compression component can be used on its own in conjunction with the data output component, or any combination of two or more of the components, and in any desired order. The separate channels may be multiplexed into less channels at any stage in order to reduce the number of potentially power hungry parallel processing paths. Part or all of the components that are implemented can be implemented in analogue and indeed it will be noted that if the final signal received by the data output component is itself analogue then the analogue signal can be transmitted rather than digitising the signal and sending a digital signal, reducing the component requirements and power consumption yet further.

The output signal can trigger a seizure outset alarm to the patient and/or physician upon recognition of an appropriate signal artefact—for example using a feature recognition circuit and/or a prevention steps can be instigated for example using a known seizure prevention device.

The approach can implement alternative approaches, for example the chopper amplifier can be replaced by an alternative noise reducing circuit.

The apparatus may be subcutaneous or otherwise implanted, and the various circuits adjusted appropriately to accommodate, for example the increased signal amplitude.

Finally, it will be appreciated that although the specific examples discussed herein are in relation to epilepsy monitoring, the invention is also applicable to other EEG applications, such as those where cognitive states such as fatigue, drowsiness, stress, workload, memory and attention are monitored. These may be of special relevance in military applications. In these cases desired data would be that containing brainwave features that are indicative of the user's cognitive state.

The invention claimed is:

1. An apparatus for obtaining EEG data comprising:
a signal processing component that receives one or more EEG signals from each of a plurality of electrodes; and
a data output component,
the signal processing component converting respective EEG signals in real time to a reduced data set and providing the reduced data set to the data output component,
wherein the signal processing component recognizes a part of the received one or more EEG signals corresponding to one or more EEG signal profiles of an expected EEG feature and provides a section of data corresponding to the recognized part to the data output component,
wherein the signal processing component includes a voltage offset removal component that removes voltage offset to reduce a number of bits of the data set,
wherein the voltage offset removal component comprises an analogue component,
wherein the analogue component comprises an analogue chopper amplifier,
wherein the analogue chopper amplifier comprises sequentially an input chopper switch circuit stage, an amplifier stage and an output chopper switch circuit stage,
wherein an effective resistance and input capacitance of the input chopper switch circuit stage and an input capacitance of the amplifier stage are configured to form a high pass filter, and
wherein the amplifier stage includes a CMOS component in weak inversion.

2. The apparatus of claim 1, wherein the apparatus is mountable on a wearer's head.

3. The apparatus of claim 1, wherein the signal processing component comprises a feature extraction component.

4. The apparatus of claim 3, wherein the feature extraction component is arranged to identify peak filter outputs and identify a corresponding input signal feature for extraction.

5. The apparatus of claim 3, wherein the feature extraction component is at least partially analogue.

6. The apparatus of claim 3, wherein the feature extraction component is configured to execute one or more local feature extraction algorithms, and wherein the one or more local feature extraction algorithms extract one or more EEG signals corresponding to the one or more EEG signal profiles.

7. The apparatus of claim 3, wherein the feature extraction component comprises a filter having an impulse response corresponding to the one or more EEG signal profiles.

8. The apparatus of claim 7, wherein the impulse response is configured to perform a wavelet transform for a mother wavelet corresponding to the one or more EEG signal profiles.

9. The apparatus of claim 7, wherein the filter having an impulse response corresponding to the one or more EEG signal profiles comprises an analogue filter.

10. The apparatus of claim 9, wherein the analogue filter having an impulse response corresponding to the one or more EEG signal profiles is implemented on a chip.

11. The apparatus of claim 9, wherein the analogue filter having an impulse response corresponding to the one or more EEG signal profiles operates at about 1.4 $\mu$W.

12. The apparatus of claim 3, wherein the feature extraction component is configured to identify and discard EEG data which fall below a detection threshold.

13. The apparatus of claim 12, wherein the detection threshold is predetermined.

14. The apparatus of claim 1, wherein the reduced data set comprises discarded EEG data that does not correspond to the one or more EEG signal profiles.

15. The apparatus of claim 1, further comprising a base station comprising a screen display, the reduced data set being viewable on the screen display.

16. The apparatus of claim 1, wherein the one or more EEG profiles indicates an epileptic event or a cognitive state selected from the group consisting of fatigue, drowsiness, stress, workload, memory, attention and sleep stage.

17. An apparatus for obtaining EEG signals and reducing a number of bits per EEG signal comprising:
   a voltage offset removal component comprising an analogue chopper amplifier that comprises sequentially an input capacitor, an input chopper switch circuit stage and an amplifier stage, wherein parasitic capacitance at an input of the amplifier stage and the input chopper switch circuit stage switches to form an effective resistance such that when combined with input capacitance a high pass filter is formed with a cut-off frequency of less than about 0.5 Hz.

* * * * *